United States Patent [19]

Beard, Jr. et al.

[11] 4,412,086

[45] * Oct. 25, 1983

[54] PROCESS FOR SEPARATING FERRIC IRON FROM CHLORINATED HYDROCARBONS

[75] Inventors: William Q. Beard, Jr.; Richard L. Wilson, both of Wichita, Kans.

[73] Assignee: Vulcan Materials Company, Birmingham, Ala.

[ * ] Notice: The portion of the term of this patent subsequent to Dec. 22, 1998, has been disclaimed.

[21] Appl. No.: 269,514

[22] Filed: Jun. 1, 1981

Related U.S. Application Data

[63] Continuation-in-part of Ser. No. 122,040, Feb. 19, 1980, Pat. No. 4,307,261.

[51] Int. Cl.$^3$ ............................................ C07C 17/38
[52] U.S. Cl. ........................................ 570/262; 203/8; 203/32; 203/38
[58] Field of Search .......................................... 570/262

[56] References Cited

U.S. PATENT DOCUMENTS

| 3,265,748 | 8/1966 | Hurt | 570/250 |
| 3,420,749 | 1/1969 | Dehn | 570/262 X |
| 3,654,093 | 4/1972 | Schexnader et al. | 570/262 X |
| 4,307,261 | 12/1981 | Beard, Jr. et al. | 570/262 |

OTHER PUBLICATIONS

Kovacic et al., "Journal American Chemical Society," vol. 81, pp. 3261–3264 (1959).

*Primary Examiner*—Robert V. Hines
*Attorney, Agent, or Firm*—Burns, Doane, Swecker & Mathis

[57] ABSTRACT

Ferric iron is removed from chlorinated hydrocarbons having less than 6 carbon atoms per molecule by intimately contacting the latter with an oil that comprises one or more hydrocarbons having at least 6 concatenated aliphatic carbon atoms per molecule. The hydrocarbon oil is present in an amount sufficient to interact with a major portion of the ferric iron. The resulting mixture of the chlorinated hydrocarbon stream and the hydrocarbon oil is heated simultaneously with the intimate contacting, and a precipitate is allowed to form. The chlorinated hydrocarbon stream is then separated from the hydrocarbon oil and from the precipitate, and the precipitate is subsequently separated from the hydrocarbon oil, which may be recycled and re-used.

17 Claims, No Drawings

PROCESS FOR SEPARATING FERRIC IRON FROM CHLORINATED HYDROCARBONS

RELATED APPLICATION

This application is a continuation-in-part of application Ser. No. 122,040 filed Feb. 19, 1980, now U.S. Pat. No. 4,307,261.

BACKGROUND OF THE INVENTION

1. Field of Invention

Valuable chlorinated hydrocarbons such as ethyl chloride, 1,1-dichloroethane, methylchloroform, and analogous chlorinated derivatives of higher hydrocarbons such as propane or butane are commonly made by liquid phase catalytic hydrochlorination of the corresponding unsaturated precursor such as ethylene, vinyl chloride or vinylidene chloride. Ferric chloride is usually used as the catalyst in such processes. However, the separation of ferric iron from chlorinated hydrocarbons has been a long-standing problem. The presence of ferric iron, particularly in the form of ferric chloride catalyst, during the flashing and recovery of the desired chlorinated hydrocarbons causes dehydrochlorination of the chlorinated hydrocarbons such as methylchloroform and subsequent polymerization of the resulting unsaturated product. Many methods have been tried for removal, deactivation and/or disposal of ferric chloride, but all have serious deficiencies.

2. State of the Art

The most obvious method of removing ferric chloride from chlorinated hydrocarbon streams is the extraction of the ferric chloride with aqueous acid solutions. The ferric chloride is unexpectedly difficult to remove in this manner. Part of the ferric chloride apparently retains some solubility in the organic layer by forming complexes with polymeric material. Furthermore, the resulting chlorinated hydrocarbon product must be dried, which is an expensive procedure on an industrial scale.

Ferric chloride has also been separated from methylchloroform by using almost anhydrous bases, such as the hydroxides of sodium, potassium, and calcium, to absorb the ferric chloride. These materials are relatively inefficient and allow easy pluggage of absorption equipment by the ferric hydroxide produced. The spent bases would constitute a difficult disposal problem. Such a separation process is described in Japanese Pat. No. 71 16,491.

German Pat. No. 1,235,878 discloses a process in which ammonia is used to precipitate ferric chloride. The ammonia is thereafter separated from the chlorinated hydrocarbon product by distillation. Ammonia has also been used in conjunction with steam to precipitate the ferric chloride while removing the chlorinated hydrocarbons by steam distillation (see U.S. Pat. No. 3,115,528). However, the use of these ammonia methods can introduce small amounts of amines as contaminants into the product. Amines or excess ammonia would be at least as undesirable as water. Moreover, steam distillation can aggravate the hydrolysis of a chlorocarbon such as methylchloroform, which is known to occur with great facility in the presence of ferric chloride and moisture.

Ferric chloride has also been removed from chlorinated hydrocarbons by sequestration of the ferric iron by a lower alkanol solution of a partial amide of ethylenediaminetetraacetic acid. Such a process is taught in U.S. Pat. No. 3,848,005. However, this process was intended primarily for the deactivation of small amounts of iron during distillation and thus would not be economical or practical for removal of the relatively large amounts of hydrochlorination catalyst.

Ferric chloride has also been removed from chlorinated hydrocarbons by contacting the chlorinated hydrocarbon streams with activated charcoal and with other porous adsorbents such as silica gel, alumina, or molecular sieves. See, for example, British Pat. No. 1,380,497 and Japanese Patent No. 72 16,801. The adsorbents, particularly activated carbon, work well in removing the iron chloride but contain water which is released to the chlorinated hydrocarbon with the concomitant undesirable effects. Moreover, regeneration of these adsorbents presents problems in corrosion and disposal, since the adsorbed iron has to be removed with an aqueous acid.

The removal of ferric chloride from chlorinated solvents has also been attempted by reduction of the ferric chloride to ferrous chloride through treatment with reducing agents such as stannous chloride, cuprous chloride, or iron, followed by distillation of the solvent, as described in U.S.S.R. Pat. No. 530,877. The use of stannous chloride or cuprous chloride presents an increased expense, and the use of iron creates an increase in the amount of ferrous chloride requiring disposal.

In U.S. Pat. No. 4,001,345 the use of quaternary ammonium salts has been proposed to inhibit the catalytic effects of ferric chloride on methylchloroform during distillation. However, because quaternary ammonium compounds are expensive, the operational cost of such a process would be high. In addition, decomposition of the quaternary ammonium salts to amines may take place.

Other prior art of interest includes the references cited in parent application Ser. No. 122,040 filed Feb. 19, 1980, now U.S. Pat. No. 4,307,261, including especially U.S. Pat. Nos. 3,265,748 (Hurt), 3,420,749 (Dehn) and 3,654,093 (Schexnayder et al), and Kovacic et al, J.A.C.S. 81, 3261-3 (195).

U.S. Pat. No. 3,654,093 relates essentially to the prevention of coke formation in non-catalytic chlorination processes or in any event in processes wherein the process liquids contain only a very small concentration of iron, e.g., iron that becomes a contaminant in the process liquids as a result of their contact with equipment surfaces. As shown in this reference, the process liquids in such cases typically contain only about 0.0004% iron, and the removal of such iron is not addressed as a problem nor solved by the reference. The reference discloses the expedient of adding an alkyl aromatic hydrocarbon to chlorinated hydrocarbons in a very small proportion, e.g., less than 1%, for the purpose of reducing coking or degradation of the desired alkyl chloride product to unwanted polychlorides and other undetermined by-products during distillation, and subsequently discarding such heavy ends including the hydrocarbon that was added as an anti-fouling agent. By contrast, the present invention deals with the problem of ridding desired chlorocarbons of potentially troublesome residual ferric chloride catalysts, which is present in such chlorocarbons in a concentration of at least 0.01%, by adding to the iron-containing chlorocarbon mixture a reactive, relatively high-boiling hydrocarbon oil in a proportion of at least about 10 volume percent. In this process, ferric chloride is reduced by reaction with the added hydrocarbon while the latter becomes dehydrogenated and converted to a free-flowing carbon-containing powder composed essentially of ferrous chloride. As a result, decomposition of valuable chlorocarbon product is minimized and a powderlike residue is produced that can be easily and safely disposed of.

U.S. Pat. No. 3,265,748 relates to a process for making ethyl chloride by the hydrochlorination of ethylene in the presence of ferric chloride catalyst and seeks to minimize unwanted side reactions such as olefin polymerization and the concomitant build-up of chlorine-containing polymeric catalyst poisons in the system. It achieves this by a special piping arrangement that permits a "disposal liquid" to be continuously purged from the system. However, no hydrocarbon oil is added and no portion of the disposal liquid is recycled in this prior art process, which is essentially a once-through process. As a result, economically important amounts of chlorine and hydrocarbon are lost. In contrast to the instantly claimed invention, the reference totally lacks in teaching an addition of any kind of high-boiling hydrocarbon oil as a medium that is instrumental in preventing any significant decomposition of desired chlorocarbon product by deactivating ferric chloride catalyst residues and removing them from the process in the form of a filtrable, environmentally safe and convenient powder.

U.S. Pat. No. 3,420,749 relates to a distillation process for purifying iron-contaminated hydrocarbon chlorides using at least one mole per mole of iron of an ester of phosphoric or phosphorous acid as a medium for forming a soluble complex iron ester, which is ultimately discarded as part of an unwanted liquid bottoms stream. While this may reduce equipment fouling in the system, it still manifestly allows substantial degradation of desired chlorocarbons and formation of unwanted high-boiling chlorides to take place. In the end, this not only results in a substantial loss of chlorocarbon product and costly ester additive, but actually aggravates the ultimate pollution problem rather than alleviating it.

The Kovacic et al paper describes a purely academic investigation of the reaction of ferric chloride with alkane, without any suggestion of its practical utility and without any particular attention to the kind of residue formed or its ultimate disposal. It totally lacks any disclosure dealing with the manufacture or processing of aliphatic chlorocarbons, much less with the problem of their degradation when they are distilled in the presence of ferric chloride or the possibility of counteracting such degradation by the addition of any other material.

Experience has shown that the disposal of ferric chloride-containing material from hydrochlorination processes poses a constant series of problems in commercial practice. A considerable amount of chlorinated hydrocarbon remains with the ferric chloride-containing material after conventional separation, making it highly corrosive. In addition, flasher fouling has caused a considerable amount of shut-down time. Moreover, increasingly stringent regulations for the disposal of hazardous landfill material have caused an increased impetus to find a more acceptable method for removing and disposing of ferric iron in hydrochlorination processes.

Thus, it is an object of the present invention to provide a process for the removal of ferric iron from hydrochlorination processes whereby the removal of ferric iron is accomplished without substantial decomposition of the chlorinated hydrocarbon product.

It is also an object of the present invention to provide a process for the removal of ferric iron from hydrochlorination processes in which fouling of the hydrochlorination apparatus is substantially reduced.

It is also an object of the present invention to provide a process for the removal of ferric iron from chlorinated hydrocarbons wherein no moisture is introduced into the system.

It is another object of the present invention to provide a low-cost process for the removal of ferric iron from chlorinated hydrocarbons, using a relatively high-boiling hydrocarbon oil as a medium in which dissolved ferric chloride is converted into a filtrable, granular precipitate.

It is still another object of the present invention to provide a process for the removal of ferric iron from hydrochlorination processes whereby the handling properties of the residues are improved.

It is a further object of the present invention to provide a process for the removal of ferric iron from hydrochlorination processes whereby the iron-containing residues are rendered non-hazardous in order to allow ordinary landfill disposal in compliance with environmental protection laws and regulations.

These and other objects, as well as the use of the invention in attaining them, will become more fully apparent from the description which follows.

SUMMARY OF THE INVENTION

The present invention provides a process for the removal of ferric iron from relatively volatile chlorinated hydrocarbons containing 1 to 5 carbon atoms per molecule. According to the invention, a $C_1$ to $C_5$ chlorinated hydrocarbon or a mixture thereof containing ferric iron is intimately contacted in liquid phase with a relatively less volatile hydrocarbon oil which comprises hydrocarbons containing at least 6 concatenated carbon atoms per molecule and having a boiling point or range at least 20° C. higher than the boiling point or range of the chlorinated hydrocarbons being treated. The less volatile oil is present in an amount sufficient to interact with a major portion of the ferric iron contained in the chlorinated hydrocarbon being treated. The resulting intimate mixture of the iron-containing chlorinated hydrocarbon and the less volatile oil is heated until a solid precipitate is formed. The volatile chlorinated hydrocarbon is then separated from the less volatile oil, for instance, by flashing or fractional distillation, and the precipitate is subsequently mechanically separated from the oil.

DETAILED DESCRIPTION OF THE INVENTION

According to the present invention, dissolved or partially dissolved ferric iron compounds, such as ferric chloride, are removed from low-boiling chlorinated hydrocarbons with virtually no decomposition of the latter. This removal is accomplished by contacting the iron-contaminated chlorinated hydrocarbons in liquid phase with a hot, relatively high-boiling oil composition comprising one or more hydrocarbons or partially chlorinated hydrocarbons or a mixture thereof. As a result, the oil chemically reduces the ferric compound to the ferrous state and thus forms a solid precipitate of iron compounds combined with a small amount of carbonaceous material that is substantially insoluble in the liquids present. Unlike conventionally separated ferric chloride catalyst residues, which tend to be deliquescent and corrosive, the precipitate obtained according to this invention is an easily filtered, granular, dark-colored solid that is non-hazardous for landfill disposal. Any adherent liquid oil can be readily removed from the precipitate by washing with a suitable solvent such as a light liquid hydrocarbon or chlorinated hydrocarbon or by stripping with an inert gas such as nitrogen prior to disposal, if desired. It is preferred to use for this purpose the same low-boiling chlorinated hydrocarbon as is used in the principal contacting step in order to permit recycling the wash liquid into the contacting step. Residual chlorinated hydrocarbon or wash liquid can be removed by heating.

The invention may be used in conjunction with any conventional hydrochlorination process which yields as a product a chlorinated hydrocarbon having less than about six carbon atoms per molecule. Such conventional hydrochlorination processes are well known in the art and need not be discussed in detail here. Typically, such processes involve the reaction of hydrogen chloride with an ethylenically-unsaturated $C_2$ to $C_5$ hydrocarbon or chlorocarbon, e.g., ethylene, propylene, pentene, vinyl chloride, vinylidene chloride, allyl chloride, 2-chloropropene, 3-chloro-1-butene, or 5-chloro-2-pentene, or with a mixture of two or more such compounds, in the presence of a ferric chloride ($FeCl_3$) catalyst. Accordingly, the product of such a hydrochlorination reaction is a saturated aliphatic chlorocarbon containing 2 to 5 carbon atoms and 1 to 3 chlorine atoms per molecule or a mixture containing two or more such compounds. The hydrochlorination reaction is ordinarily conducted in liquid phase.

Although other Friedel-Crafts catalysts, such as aluminum chloride and zinc chloride, may be used in typical hydrochlorination processes, such catalysts are not included within the scope of the present invention. When removed from chlorinated hydrocarbons by the process of the present invention, aluminum chloride and zinc chloride would remain hygroscopic, corrosive, and chemically reactive after separation. Ferric halide is therefore unique. Being multivalent, it is chemically reduced by the oil to produce essentially an inert, harmless, easily disposable solid.

In its preferred embodiment, the invention is directed particularly toward the removal of ferric iron from the hydrochlorination reactor product obtained in the manufacture of methylchloroform. In such a process, a chlorocarbon mixture comprising primarily vinyl chloride together with some vinylidene chloride is hydrochlorinated to 1,1-dichloroethane and 1,1,1-trichloroethane (methylchloroform), respectively. Of course, the invention is also applicable when an individual compound such as only vinyl chloride or only vinylidene chloride is hydrochlorinated.

The chlorinated hydrocarbon which is contacted with hot oil according to the present invention comprises the liquid product stream from a typical hydrochlorination process. This chlorinated hydrocarbon product typically contains ferric iron, e.g., ferric chloride ($FeCl_3$), either dissolved therein or suspended therein as a finely divided solid or it may be present both in solution and in suspension. Depending on the nature of the feed to and the conversion in the hydrochlorination reaction, this chlorinated hydrocarbon comprises either one or a plurality of $C_1$ to $C_3$ chlorinated hydrocarbons. According to a preferred embodiment, the iron-contaminated chlorinated hydrocarbon to be treated comprises a mixture of 1,1-dichloroethane and 1,1,1-trichloroethane (methylchloroform).

The iron-contaminated chlorinated hydrocarbon liquid is contacted with a hydrocarbon oil or partially chlorinated hydrocarbon oil that has a boiling range substantially higher than the boiling point or range of the chlorinated hydrocarbon liquid. The oil may comprise one or more hydrocarbons having at least six concatenated carbon atoms, e.g., $C_6$ to $C_{40}$ or higher hydrocarbons. Oil compositions containing an average of at least 12 and up to 40 carbon atoms per molecule have produced excellent results to date. The hydrocarbons may comprise alkanes, alkenes, alkyl benzenes, alkyl naphthalenes, cycloalkanes, cycloalkenes or the like, or mixtures of two or more of such hydrocarbons or kinds of hydrocarbons. When alkylated aromatics are used as the reducing oil, it is preferred to use oil compositions comprising a major or at least a substantial proportion of aromatic compounds having at least one aliphatic side chain containing six or more carbon atoms, e.g., n-hexyl benzene, nonylnaphthalene, etc. Cycloalkenes such as cyclohexene or cyclooctene are also effective in reacting with the ferric iron.

Examples of commercially available hydrocarbon oils which are suitable for the purposes of this invention include Sontex-55NF (Marathon Morco), Soltrol-220 (Phillips Petroleum), Peneteck (Penreco), Nalkylene-500 (Conoco), USP Mineral Oil (Squibb), and n-dodecane (Phillips Petroleum). Other commercial white mineral oil products are also suitable. Hydrocarbon oil compositions composed predominantly of saturated aliphatic hydrocarbons are currently thought to be preferred. Specifications of suitable oil compositions tested are shown in Table I.

TABLE I

| | Specifications of Mineral Oils Tested | | | | |
|---|---|---|---|---|---|
| | n-Dodecane | USP Min. Oil | Sontex-55NF | Soltrol-220 | Peneteck |
| Source | Phillips | Squibb | Marathon Marco | Phillips | Penreco |
| Boiling range (°F.) | 417 | — | — | 460–495 | 516 |
| Viscosity (SUS 100° F.) | a | 178[b] | 55 | 38.5 | 38–42 |
| Flash point (°F.) | 165 | — | 325 | 229 | 265 |
| Specific gravity 60/60° F. | 0.751 | 0.882 | 0.840 | 0.810 | 0.804–0.816 |
| Pour point (°F.) | — | — | +10 | — | +35 |
| Avg. molecular weight | 170 | 390[c] | 283 | 198 | 212 |
| Percent paraffins | 100 | — | 65.5 | — | — |
| Percent naphthenes[d] | 0 | — | 34.5 | — | — |
| Avg. carbon no. | $C_{12}$ | $C_{29}$[c] | $C_{20}$ | $C_{14}$ | $C_{15}$ |

[a]1.257 centipoise at 23.3° C.
[b]USP minimum specification
[c]Estimate for white mineral oils based on viscosity and specific gravity
[d]Naphthenes - saturated cyclic hydrocarbons The exact nature of the chemical reaction between the oil and the ferric salt is not definitely known, and the present invention is not necessarily predicated on any particular reaction mechanism. However, possible mechanisms may be similar to those discussed by Kovacic et al in J. Am. Chem. Soc., 81, 3261 (1959) and in J. Org. Chem. 28, 2551 (1963).

According to the present invention, a chlorinated hydrocarbon product containing ferric iron and comprising one or more relatively low-boiling chlorinated hydrocarbons is intimately contacted or mixed with a relatively higher boiling oil, as defined above. The oil is present in an amount at least sufficient to interact with a major portion of the ferric iron, e.g., sufficient to reduce at least 60% and preferably at least 95% of the iron present to the divalent state. Any proportion of oil to iron-containing chlorinated hydrocarbon can be used with good results as long as the volume of oil is sufficient to provide for intimate contact with the iron halide that is disperse and/or dissolved in the chlorocarbon, but only a very small amount of the oil is actually required to effect the desired chemical reaction and cause the desired precipitate to form.

Typically, for instance, the chlorocarbon to be treated may contain from 0.01 to 3% ferric chloride catalyst by weight, although compositions containing lower or higher concentrations of ferric halide catalyst may be treated in accordance with this invention. Conveniently, the ratio of oil to chlorocarbon in the contacting zone is maintained between about 10 and about 10,000 volumes of oil per 100 volumes of iron-containing chlorocarbon, preferably between about 30 to about 500 volumes of oil per 100 volumes of the chlorocarbon. Of course, it should be understood that, for instance, when the treatment is conducted in a flash pot, a given batch of the oil may remain in the port almost indefinitely while the iron-containing chlorocarbon composition is fed into it on a continuous basis and the volatile chlorocarbon is flashed off almost instantaneously and withdrawn from the pot. In such a case, the volume of oil used in the process relative to the volume of chlorocarbon treated in the process over an extended time is almost nil.

The resulting mixture of the chlorinated hydrocarbon and the hydrocarbon oil is heated while maintaining intimate contact between the chlorinated hydrocarbon and the oil. In order to ensure interaction of the ferric iron and the hydrocarbon oil, the mixture is heated to a temperature of at least 30° C. Such heating may be under reflux or under pressure to prevent the escape of the relatively volatile product, or the product may be simultaneously distilled off. The mixture is preferably heated to a temperature of between about 60° and 140° C., and, more preferably, to a temperature of between about 100° and 130° C. In the most preferred embodiment of the invention, the mixture is heated to a temperature of between about 110° and 120° C.

The optimum temperature and residence time of the thermal treatment of course depends to some extent on the chemical characteristics of the particular reducing oil used, the concentration of ferric iron present in the chlorinated hydrocarbon and the proportion of oil to the chlorinated hydrocarbon, but optimum conditions can be readily and routinely determined for any given case by preliminary empirical tests.

While the chlorinated hydrocarbon and the oil are contacted and heated, a precipitate is formed. This precipitate forms as the result of the interaction between the ferric iron and the hot oil. Although the exact nature of this interaction is presently unknown, it has been found that this essentially insoluble precipitate is a composition in which the iron is present predominantly in the divalent state, e.g., as $FeCl_2$, combined either chemically or physically with a small amount of carbonaceous material from the high-boiling oil. The precipitate forms as an easily filtered, dark-colored solid. It is neither hygroscopic nor corrosive, and is therefore non-hazardous for landfill disposal. Such characteristics are distinctly advantageous in light of the concern for the protection of the environment from hazardous wastes. Note, for instance, the Resource Conservation and Recovery Act. "Spent catalyst from hydrochlorinator reactor in the production of 1,1,1-trichloroethane" has been specifically listed in 44 Federal Register 49403, Aug. 22, 1979, Section 250.14(b)(2), as a possible source of hazardous waste.

During the formation of the precipitate, there is no build-up of impurities from the interaction of the hot oil with the ferric iron. The interaction apparently proceeds to the point where all contaminants become part of the precipitate. Thus, a batch of oil may last almost indefinitely, until it is all converted to precipitate, although of course a sufficient volume of liquid oil must be present in the contacting zone, e.g., a flash pot, to provide for contact with the iron-containing chlorocarbon that is fed into the zone either batchwise or continuous and flashed off. There is no indication that the chlorinated hydrocarbon product stream contributes to the precipitate under normal circumstances.

As or after the precipitate has formed, the low-boiling chlorinated hydrocarbon stream is separated from the higher boiling oil and solid precipitate. This can be accomplished by ordinary distillation or more conveniently by flash distillation either in the original treating zone or after transfer to a separate distillation tower, batchwise or continuously, or in any other suitable manner. The residue containing the oil and precipitate can be mechanically separated in any suitable manner, such as filtration or centrifugation. The separation may be accomplished either continuously or periodically. Following separation, adsorbed oil can be removed from the filter cake by stripping with a substantially inert gas, preferably hot nitrogen, or by washing with a liquid solvent, preferably using for this purpose a portion of the low-boiling chlorinated hydrocarbon that has been recovered from the separation step, or solvent washing and gas stripping may be employed in sequence. Following such washing with the chlorinated hydrocarbon, the recovered chlorinated wash liquid can be recycled to the contacting step. Alternatively, any other non-noxious wash solvent such as petroleum naphtha, decane, benzene, toluene or other relatively low-boiling $C_5$ to $C_{10}$ hydrocarbon solvent may be used and the resulting wash liquid disposed of in whatever manner may be convenient at the particular location and in the particular circumstances.

For instance, such wash liquid can be fractionally distilled and the resulting higher-boiling oil fraction can be recycled to the previously mentioned flash pot and the resulting solvent fraction can be re-used in washing additional portions of oil-containing filter coke. If desired, residual solvent remaining in the precipitate after such washing may be stripped therefrom with an inert gas, such as cold or hot nitrogen or steam, and recovered for further use.

When the process of the present invention is practiced as described herein, the percentage dehydrochlorination of the chlorinated hydrocarbon product is too small to measure conveniently. That is, ferric iron is removed from chlorinated hydrocarbon streams without any significant decomposition of the chlorinated hydrocarbon product. Furthermore, no noticeable tarry or polymeric decomposition products of the chlorinated hydrocarbon are formed, as shown by the powdery character of the solid precipitate and its ease of separation from the oil. The weight of precipitate obtained is usually of the same order as the weight of ferric chloride initially present, and the consumption of oil is virtually inconsequential. The dried precipitate contains no volatile solvent, is not corrosive, is not hygroscopic, and is, therefore, easily handled. An additional advantage is that no moisture is introduced so that no subsequent solvent-drying step is required.

A preferred embodiment of the present invention comprises continuously feeding a liquid chlorinated hydrocarbon stream containing ferric chloride catalyst from a hydrochlorination reaction to a flash distillation pot which contains a relatively high-boiling hydrocarbon oil that is held at sufficiently high temperature to distill off the chlorinated hydrocarbon and to achieve rapid reaction of the ferric chloride with the oil as the chlorinated hydrocarbon composition enters the flash distillation pot and is intimately mixed there with the oil. Since the chlorinated hydrocarbon, e.g., a mixture of 1,1-dichloroethane and methylchloroform, is almost immediately flashed from the vessel, only a low concentration of chlorinated hydrocarbon is normally maintained in the pot at any time. The iron is constantly precipitated as a relatively fine, dark-colored powder which can be easily removed in any convenient manner, either periodically or continuously, as described above.

The following examples are given as specific illustrations of the invention. It should be understood, however, that the invention is not limited to the specific details set forth in the examples.

EXAMPLE I

The treating vessel was a dried 250-ml. round-bottom flask equipped with a heating mantle, a magnetic stirrer, and a thermocouple connected to a temperature controller. To the reaction flask was attached a distilling head, condenser, receiver, and an addition funnel for adding the liquid chlorinated hydrocarbon which contained ferric chloride. As shown in Table II below, 100 ml. portions of various hydrocarbon oils were charged to the flask after it had been swept with nitrogen. The specific gravities of these oils varied from 0.740 to 0.882. After the oil had been treated to the indicated temperature, the iron-containing liquid chlorinated hydrocarbon was added at a substantially uniform rate over the period of time shown in the table.

The chlorinated hydrocarbon was predominantly 1,1-dichloroethane together with the amounts of 1,1,1-trichloroethane indicated in Table II. In Run No. 3, a single 550 g portion of chlorinated hydrocarbon was actually used but was continuously recycled about 27 times, with fresh $FeCl_3$ being added to the recycle before introduction to the treating vessel.

After all of the chlorinated hydrocarbon liquid had been added to and flashed off from the hydrocarbon oil, the hot oil was filtered through a sintered glass funnel under slight pressure to remove the solid precipitate. The solids were stirred and washed with hexane or other solvent to remove adsorbed oil, which was subsequently recovered from the hexane. The dried, dark solid was weighed and analyzed. The data for the recovered liquids set out in Table II for Run No. 3 were based on the original chlorinated hydrocarbon charge. The losses of chlorinated hydrocarbon amounted to 0.20% 1,1-dichloroethane and 0.36% 1,1,1trichloroethane per recycle.

Virtually all of the chlorinated hydrocarbon was recovered without dehydrochlorination or tar formation on a single pass through the flasher. Infrared analysis of the hydrocarbon oils showed no build-up of soluble impurities. The solids in all runs were dry and powdery and not hygroscopic or corrosive. In Run No. 3, where sufficient material was used to ensure accuracy, the weight of solid was 91% of the weight of ferric chloride initially added, and the precipitate consisted largely of ferrous chloride ($FeCl_2$ contains 44% Fe). The precipitate would always weigh 78% of the amount of ferric chloride initially present if the precipitate were only ferrous chloride. The data indicate that the precipitate itself contained, on a weight basis, about 81 $FeCl_2$ and about 19% contaminant such as, carbon, polymer, etc. The total quantity of precipitate requiring disposal is less than the total quantity of $FeCl_3$ catalyst present to the hydrochlorination step and is thus very small.

TABLE II

Flashing of Ferric Chloride-Containing Mixtures of Chlorinated Hydrocarbon Compositions From Various Oils

| Run No. | 1 | 2 | 3 |
|---|---|---|---|
| Hydrocarbon oil | n-Dodecane | USP Mineral Oil (Squibb) | Sontex-55NF (Marathon Morco) |
| Average carbon no. | $C_{12}$ | $C_{29}$ | $C_{22}$ |
| Estimated initial b.p. (°C.) | 214 | 450 | 370 |
| Weight (g) | 75.1 | 88.2 | 82.6 |
| Chlorinated Hydrocarbon | | | |
| Weight (g) | 233 | 277 | 14542 |
| 1,1-Dichloroethane (%) | 84.7 | 84.8 | 84.0 |
| 1,1,1-Trichloroethane (%) | 15.3 | 15.2 | 16.0 |
| Ferric chloride (ppm) | 1320 | 1508 | 688 |
| Oil temperature (°C.) | 110 | 120 | 115 |
| Duration of run (hrs) | 0.75 | 0.9 | 44.8 |
| Recovered liquids (%) | | | |
| Oil | 99.7 | 100 | 100 |
| 1,1-Dichloroethane | 98.8 | 98.7 | 94.6 |
| 1,1,1-Trichloroethane | 97.2 | 99.2 | 90.3 |
| % Oil in distillate | 1.86 | — | 0.01 |
| Recovered solids | | | |
| Dried solids (g) | 0.35 | 0.48 | 9.12 |
| Wt ratio Solids Out/$FeCl_3$ In | 1.13 | 1.50 | 0.91 |
| Analysis of recovered solid | | | |
| Fe (wt %) | — | 21.88 | 34.72 |
| Cl (wt %) | — | — | 46.19 |
| Cl/Fe (molar) | — | — | 2.09 |

EXAMPLE II

A simple rapid screening method for prospective oils was devised which involved the determination of whether ferric chloride would react rapidly with the oil (no chlorinated hydrocarbon present) and form a manageable precipitate. All of the hydrocarbon oils evaluated by this method successfully passed the test. Three of the oils so tested were also employed in separation runs with chlorinated hydrocarbons, as reported in Table I, thereby confirming the validity of the screening method.

The treating vessel was a dried 250-ml, round-bottom flask equipped with a heating mantle, a magnetic stirrer, and a thermocouple connected to a temperature controller. To the reaction flask was attached a vapor take-off to a fluorocarbon bubbler and a water trap for absorbing evolved hydrogen chloride. A nitrogen purge inlet was fitted to the body of the flask. As shown in Tables III and IV below, 100-ml portions of various hydrocarbon oils with or without small amounts of additives were charged to the flask after it had been swept with nitrogen. The specific gravities of the oils varied from 0.740 to 0.882. With the oil still at room temperature, a 10-g portion (40-g in the case of Run Number 1, Table III) of ferric chloride, handled to exclude moisture, was added to the flask. The equipment was sealed and the reactants were heated to the final temperature with stirring over a period of about thirty minutes. The temperature where significant evidence of reaction (gas evolution or color change) began was recorded as the activation temperature.

At the end of the period the system was purged well with nitrogen through the water trap to insure absorbance of all evolved hydrogen chloride. The yield of hydrogen chloride was determined by titration of the trap, and the percentage yield was based on a theoretical yield of one mole per mole of ferric chloride. The solid was collected on a filter, washed with dry hexane, dried and weighed. The oil was recovered, including that from the hexane washings.

The tests in Table III indicate that alkanes and mixtures of alkanes as well as olefins and alkylated aromatics containing an aliphatic moiety of at least six carbon atoms per molecule react rapidly with ferric chloride at low temperatures, in some cases below 30° C. and with many of the preferred oils at between about 30° C. and about 75° or 100° C., and give easily managed precipitates. Tests in Table IV show the reactivity of ferric chloride with partially halogenated and olefinic derivatives of long-chain alkanes even in the presence of large amounts of an alkane. In fact, the ferric chloride sometimes reacts with these derivatives preferentially.

TABLE IV

Screening Tests For Reaction of Ferric Chloride with Olefins and Chlorinated Hydrocarbons in Dodecane

| Run no. | 1 | 2 |
|---|---|---|
| Hydrocarbon oil | n-Dodecane (75.1 g) | n-Dodecane (75.1 g) |
| Additives | 2% Decene-1 | 1.2% 2-chlorooctane 0.8% Octenes |
| Wt FeCl$_3$, g | 10.0 | 10.0 |
| Final Temp., °C. | 125 | 100 |
| Time at final temp. (hrs) | 0.5 | 2.3 |
| Yield of HCl, %[a] | 82.0 | 82.1 |
| Recovered oil, %[b] | | |
| Dodecane | 99.1 | 99.3 |
| Decene-1 | 6.3 | — |
| 2-Chlorooctane | — | 8.3 |
| Octenes | — | 27.2 |
| Recovered solids | | |
| Dried solids, g | 8.87 | 9.13 |
| Wt ratio: Solids out/FeCl$_3$ in | 0.887 | 0.913 |
| Total mass accountability, % | 98.4 | 99.1 |

[a] Yield of HCl based on a theoretical maximum of one mole of HCl per mole of ferric chloride.
[b] Recovery of each component is stated as a percentage of the original amount present.

It is to be understood that the foregoing detailed description is given merely by way of illustration and that many variations may be made therein without departing from the spirit or scope of the invention claimed below.

What we claim is:

1. A process for the removal of ferric chloride from chlorinated aliphatic hydrocarbons having less than 6 carbon atoms per molecule, comprising the steps of:
(a) mixing a liquid comprising a major amount of at least one relatively volatile saturated aliphatic chlorinated hydrocarbon having 2 to 5 carbon atoms per molecule and at least 0.01% of ferric chloride admixed therewith, with at least 10 volumes (per 100 volumes of volatile chlorinated hydrocarbon) of a relatively less volatile oil composition comprising a hydrocarbon having at least 6 concatenated aliphatic carbon atoms per molecule

TABLE III

Screening Tests with Various Oils for Reaction with Ferric Chloride

| Run No. | 1 | 2 | 3 | 4 | 5 | 6 | 7 |
|---|---|---|---|---|---|---|---|
| Hydrocarbon oil | n-Dodecane Phillips | USP Min. Oil Squibb | Sontex-55NF Min. Oil Marathon Morco | Soltrol-220 Phillips | Peneteck Penreco | 1-Decene Aldrich | Nalkylene 500(Conoco) |
| Avg. carbon no. | C$_{12}$ | C$_{29}$ | C$_{20}$ | C$_{14}$ | C$_{15}$ | C$_{10}$ | C$_{18}$ |
| Nature of oil | Alkane | White Min. Oil | White Min. Oil | Branched Alkane | White Min. Oil | Olefin | Dodecylbenzene |
| Ext. initial b.p., °C. | 214 | 450 | 370 | 238 | 269 | 172 | — |
| Weight, g | 75.1 | 88.2 | 82.6 | 79.2 | 80.9 | 74.0 | 85.8 |
| Weight FeCl$_3$, g | 40.0 | 10.0 | 10.0 | 10.0 | 10.0 | 10.0 | 10.0 |
| Activation temp.[a] | ca 100 | ca 100 | 35–40 | 50–60 | 72 | 30 | 30–33 |
| Final temp., °C.[b] | 120 | 135 | 125 | 120 | 120 | 100 | 115 |
| Time at final temp., hrs | 2.0 | 3.0 | 1.5 | 0.5 | 2.0 | 2.0 | 0.25 |
| Yield of HCl, %[d] | 79.6 | 70.9 | 79.9 | 74.9 | 72.5 | 0.0[c] | 77.9 |
| Recovered oil, % | 96.1 | 96.3 | 98.8 | 94.7 | 98.8 | — | — |
| Recovered solids | | | | | | | |
| Dried solids, g | 34.29 | 9.0 | 9.04 | 8.8 | 8.11 | 8.23 | 9.01 |
| Wt. ratio: solids out/FeCl$_3$ in | 0.857 | 0.900 | 0.904 | 0.880 | 0.811 | 0.823 | 0.901 |
| Analysis of recovered solid | | | | | | | |
| Fe, wt % | 42.55 | 34.30 | 39.14 | 37.56 | 37.12 | 41.63 | — |
| Cl, wt % | 50.22 | 47.10 | 48.67 | 48.11 | 48.47 | 51.19 | — |
| Cl/Fe molar ratio | 1.86 | 2.16 | 1.96 | 2.02 | 2.06 | 1.94 | — |
| Total mass accountability, % | 98.7 | 97.3 | 99.8 | 95.9 | 98.6 | 99.3 | — |

[a] Temperature where vigorous reaction began
[b] Evidence of reaction had usually ceased by the time this temperature was reached.
[c] Although no HCl was evolved, a color change occurred which was complete by final temperature.
[d] Yield of HCl based on a theoretical maximum of one of HCl per mole of ferric chloride.

and selected from the group consisting of alkanes, cycloalkanes, alkenes, cycloalkenes, alkyl aromatic hydrocarbons, and mixtures of at least two of the foregoing;

(b) heating the resulting mixture at a temperature between about 60° and about 140° C. until a major portion of said ferric chloride is reduced to the divalent state and an easily filtrable, essentially inert, non-hazardous, powdery solid precipitate consisting largely of ferrous chloride combined with a small amount of carbonaceous material is formed without significant decomposition of said chlorinated hydrocarbon;

(c) separating said chlorinated hydrocarbon as a vapor from said oil composition and from said precipitate; and (d) mechanically separating said oil composition from said precipitate.

2. The process of claim 1, wherein said chlorinated hydrocarbon liquid comprises a chlorocarbon containing 2 to 5 carbon atoms and 1 to 3 chlorine atoms per molecule.

3. The process of claim 1, wherein said chlorinated hydrocarbon liquid consists essentially of a compound selected from the group consisting of 1,1-dichloroethane, 1,1,1-trichloroethane and of mixtures thereof and contains 0.01 to 3% ferric chloride.

4. The process of claim 3, wherein said oil composition consists essentially of saturated hydrocarbons having at least an average of 12 carbon atoms per molecule.

5. The process of claim 3, wherein said mixture is maintained at a temperature between about 100° and 130° C. and sufficient to distill off said chlorinated aliphatic hydrocarbon from said mixture by flash distillation.

6. The process of claim 5, wherein said mixture is heated to a temperature of between about 110° and about 120° C.

7. The process of claim 1, wherein said precipitate is separated from said oil composition by continuous filtration.

8. The process of claim 1, wherein said precipitate is separated from said oil composition by periodic filtration.

9. A process for the removal of ferric chloride catalyst from a liquid composition comprising a relatively volatile chlorinated saturated aliphatic hydrocarbon containing 2 to 5 carbon atoms and 2 to 3 chlorine atoms per molecule, comprising the steps of:

(a) continuously adding in a flash zone a relatively volatile chlorinated hydrocarbon liquid containing 0.01 to 3% ferric chloride catalyst admixed therewith resulting from the catalytic hydrochlorination of a member of the group consisting of ethylene, propylene, vinyl chloride, vinylidene chloride and mixtures thereof, to a body containing at least 10 volumes (per 100 volumes of said volatile chlorinated hydrocarbon present) of a relatively less volatile oil comprising a hydrocarbon containing at least 6 concatenated aliphatic carbon atoms per molecule and having at least an average of 12 carbon atoms per molecule and selected from the group consisting of alkanes, alkenes, cycloalkanes, alkyl aromatic hydrocarbons, and mixtures of at least two of the foregoing, and maintaining said body at a temperature in the range between 60° and 140° C. and which is substantially below the boiling range of said oil and above the boiling point of said relatively volatile chlorinated hydrocarbon liquid whereby the latter is flashed off and until at least 60% of the ferric iron present is converted to the divalent state and an easily filtrable, essentially inert, powdery, non-hazardous precipitate consisting largely of ferrous chloride combined with a small amount of carbonaceous material is formed in said oil by interaction of said ferric chloride with said oil;

(b) continuously removing said chlorinated hydrocarbon from said zone in a vapor form and recovering the same, leaving behind a mixture of oil and said precipitate; and (c) mechanically separating a liquid oil fraction from said solid precipitate.

10. The process of claim 9, wherein said oil is composed of predominantly aliphatic hydrocarbons having a boiling range at least predominantly above about 180°.

11. The process of claim 10, wherein said mixture of oil and ferric chloride is held in said flash zone at a temperature in the range of from about 110° to 120° C.

12. The process of claim 10, wherein said oil is one having a boiling range predominantly above 200° C.

13. The process of claim 10, wherein said oil is composed predominantly of paraffins having an average of from about 12 to about 40 carbon atoms per molecule.

14. The process of claim 10, wherein said oil fraction is separated from said precipitate by filtration.

15. The process of claim 10, further comprising the step of washing residual adsorbed oil from the separated precipitate with a non-noxious wash solvent prior to disposal of the resulting washed precipitate.

16. The process of claim 15, wherein said wash solvent is a relatively low-boiling $C_5$ to $C_{10}$ hydrocarbon and wherein the resulting wash liquid is separated by distillation into a relatively high boiling oil fraction and a relatively low boiling solvent fraction, and the oil fraction is returned to the flash zone.

17. The process of claim 15, wherein residual wash solvent is removed from said washed precipitate by stripping the same with a hot inert gas prior to disposal.

* * * * *

UNITED STATES PATENT AND TRADEMARK OFFICE
CERTIFICATE OF CORRECTION

PATENT NO. : 4,412,086
DATED : Oct. 25, 1983
INVENTOR(S) : Beard, Jr. et al.

It is certified that error appears in the above-identified patent and that said Letters Patent is hereby corrected as shown below:

Column 6, Line 53, (Table I, column 3 of the Table), "Marco" should be --Morco--.

Column 7, Line 18, "disperse" should be --dispersed--;
Line 34, "port" should be --pot--.

Column 9, Line 50, "treated" should be --heated--.

Column 10, Line 36, in Table II, Run No. 3, "$C_{22}$" should be --$C_{20}$--, consistent with the average carbon number disclsoed for the Sontex-55NF oil in Tables I & III.

Signed and Sealed this

Thirteenth Day of March 1984

[SEAL]

Attest:

GERALD J. MOSSINGHOFF

Attesting Officer

Commissioner of Patents and Trademarks